United States Patent
Rise et al.

(10) Patent No.: US 9,517,097 B2
(45) Date of Patent: Dec. 13, 2016

(54) LOW-PROFILE, HIGH TENSION MESH PLATE FOR SUBCUTANEOUS FRACTURE FIXATION

(71) Applicants: Leroy Rise, Santa Fe, NM (US); Christina Salas, Albuquerque, NM (US); Aaron Dickens, Albuquerque, NM (US); Mahmoud Reda Taha, Albuquerque, NM (US)

(72) Inventors: Leroy Rise, Santa Fe, NM (US); Christina Salas, Albuquerque, NM (US); Aaron Dickens, Albuquerque, NM (US); Mahmoud Reda Taha, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 301 days.

(21) Appl. No.: 14/255,708

(22) Filed: Apr. 17, 2014

(65) Prior Publication Data

US 2014/0316472 A1    Oct. 23, 2014

Related U.S. Application Data

(60) Provisional application No. 61/812,978, filed on Apr. 17, 2013.

(51) Int. Cl.
*A61B 17/80* (2006.01)

(52) U.S. Cl.
CPC ....... *A61B 17/8085* (2013.01); *A61B 17/8004* (2013.01); *A61B 17/8061* (2013.01)

(58) Field of Classification Search
CPC ...................................... A61B 17/80–17/8095
USPC ................................................. 606/280–299
See application file for complete search history.

(56) References Cited

U.S. PATENT DOCUMENTS

| | | | | | |
|---|---|---|---|---|---|
| 4,905,679 A | * | 3/1990 | Morgan | ............ | A61B 17/8085 227/156 |
| 5,468,242 A | * | 11/1995 | Reisberg | ............ | A61B 17/8085 606/151 |
| 5,690,631 A | * | 11/1997 | Duncan | ............... | A61B 17/8085 606/281 |
| 5,752,958 A | * | 5/1998 | Wellisz | ............... | A61B 17/8085 606/280 |
| 5,766,176 A | * | 6/1998 | Duncan | ............... | A61B 17/8085 606/281 |
| 5,814,048 A | * | 9/1998 | Morgan | ............ | A61B 17/8085 606/283 |
| 5,980,540 A | * | 11/1999 | Bruce | ................ | A61B 17/8085 606/151 |
| 6,071,291 A | * | 6/2000 | Forst | .................. | A61B 17/8085 606/151 |
| 6,093,188 A | * | 7/2000 | Murray | ............... | A61B 17/8004 606/282 |

(Continued)

*Primary Examiner* — Christian Sevilla
*Assistant Examiner* — Eric S Gibson
(74) *Attorney, Agent, or Firm* — Keith A. Vogt; Vogt IP (57) ABSTRACT

A fixation device and method for the subcutaneous fixation of bone fragments. A fixation mesh is formed by the intersection of a plurality of linear legs that are interconnected in sagittal planes to form linear sagittal lines and a plurality of crimped legs that are interconnected in transverse planes to form transverse lines. The mesh resists expansive forces that are created in the linear sagittal lines and a compressive stress is created in the transverse lines when tensile loads are applied to the linear sagittal lines resulting in a device that minimizes the gap distance between bone fragments.

22 Claims, 4 Drawing Sheets

(56) References Cited

U.S. PATENT DOCUMENTS

| | | | | |
|---|---|---|---|---|
| 7,655,047 B2* | 2/2010 | Swords | A61B 17/8085 623/17.18 |
| 8,246,663 B2* | 8/2012 | Lovald | A61B 17/8071 606/280 |
| 8,298,292 B2* | 10/2012 | Swords | A61B 17/8085 623/23.72 |
| 8,702,763 B2* | 4/2014 | Lin | A61B 17/8085 606/284 |
| 8,834,534 B2* | 9/2014 | Impellizzeri | A61B 17/8085 606/282 |
| 9,125,698 B2* | 9/2015 | Miller | A61B 17/8019 |
| 9,220,597 B2* | 12/2015 | Engstrand | A61F 2/28 |
| 2002/0173854 A1* | 11/2002 | Amrich | A61B 17/8085 623/23.53 |
| 2005/0149032 A1* | 7/2005 | Vaughen | A61B 17/8085 606/77 |
| 2005/0261780 A1* | 11/2005 | Heino | A61B 17/8085 623/23.51 |
| 2005/0288790 A1* | 12/2005 | Swords | A61B 17/8085 623/17.19 |
| 2006/0058796 A1* | 3/2006 | Hartdegen | A61B 17/1728 606/281 |
| 2006/0224242 A1* | 10/2006 | Swords | A61B 17/8085 623/17.19 |
| 2007/0238069 A1* | 10/2007 | Lovald | A61B 17/8071 433/173 |
| 2009/0099409 A1* | 4/2009 | Luehrs | A61B 17/8085 600/37 |
| 2011/0152932 A1* | 6/2011 | Wang | A61B 17/7059 606/246 |
| 2013/0090694 A1* | 4/2013 | Norris | A61F 2/30739 606/281 |
| 2014/0228969 A1* | 8/2014 | Engstrand | A61F 2/28 623/23.47 |
| 2014/0316472 A1* | 10/2014 | Rise | A61B 17/8085 606/281 |
| 2015/0105806 A1* | 4/2015 | Dorafshr | A61F 2/2875 606/151 |
| 2015/0257801 A1* | 9/2015 | Palmer | A61B 17/8004 606/281 |
| 2015/0374497 A1* | 12/2015 | Engstrand | A61F 2/2846 623/17.19 |

* cited by examiner

LOW-PROFILE, HIGH TENSION MESH PLATE FOR SUBCUTANEOUS FRACTURE FIXATION

CROSS-REFERENCE TO RELATED APPLICATIONS

This application claims the benefit U.S. Provisional Application. No. 61/812,978, filed Apr. 17, 2013 and herein incorporated by reference,

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

Field of the Invention

The present invention concerns a design that provides a low-profile mesh plate for subcutaneous, superficial bones such as the patella (knee cap), olecranon process of the ulna (elbow), and the sternum (breastbone), and other applications, that can optimally resist high tensile physiologic biomechanical stresses across a fracture site until bony union is achieved.

BRIEF SUMMARY OF THE INVENTION

The patella and patellar attachments are crucial for maximizing function of the knee extensor mechanism. There are numerous methods of fixation described in the orthopedic literature for treating patella fractures. One challenging aspect of patella fixation is the subcutaneous position of the bone. The need for secondary surgeries related to prominent and symptomatic implants has been reported in excess of fifty percent. As health care costs continue to rise, reducing the need for second surgery could significantly temper and reduce medical waste. An ideal implant for patella fixation is a low profile plate able to withstand high tensile stresses necessary to expedite postoperative rehabilitation until sufficient healing occurs.

Fracture fixation of the olecranon process of the ulna is another challenging orthopedic repair. Many types of fixation devices—suture, wire, plates, nails, and prosthetics—have been developed to maintain high tensile loads from the triceps brachii muscle, anconeus muscle, and flexor carpi ulnaris muscles. Plate fixation is recommended for highly comminuted (multi-fragmented) fractures, but the subcutaneous nature of the elbow can result in second surgeries due to symptomatic implants.

Fractures of the sternum are caused by blunt force chest injury or weakened bone from pathological disease. Unlike the patella or ulna, fractures to the sternum can lead to associated damage to internal organs such as the heart and lungs. In high impact injury, the sternum can be highly fragmented and difficult to repair with conventional wiring or plating techniques which do not allow for capture of small fragments. The subcutaneous nature of the sternum additionally limits fixation to thin cerclage wiring which is incapable of multifragmented fracture repair. Current options include rigid plate fixation with discrete screw placement options and fixed geometry.

The present invention, in a preferred embodiment, provides a solution to the above needs by providing an innovative mesh plate designed to resist physiological high tensile biomechanical stresses for subcutaneous bone fracture fixation. For example, using the devices and methods of the present invention, the mean gap distance for bone fractures in constructs immediately prior to failure was significantly smaller than tension band wire constructs. The present invention limited gaps to 3 millimeters or less. As a result, the present invention provides a low-profile design that may reduce the need for secondary surgeries related to prominence of traditional fixation constructs. The device can he shaped to precisely fit the bony contour of many anatomical structures and offers multiple holes for screw fixation of comminuted fracture fragments. By providing crimped horizontal segments of the plate, the device acts to compress fragments in a horizontal or transverse plane when vertical tension is applied across the straight segments in a sagittal plane. The design will improve the overall inherent stability of the construct, especially for fractures with multiple comminuted fragments. As a result, the low profile, high-tension mesh of the present invention is a viable option for the treatment of simple and complex fractures and has significant benefits over traditional forms of fixation.

DETAILED DESCRIPTION OF THE INVENTION

This description is not to be taken in a limiting sense, but is made merely for the purpose of illustrating the general principles of the invention. For example, one of the preferred embodiments described in detail below concerns the repair of a fractured patella. However, the scope of the invention is defined by the appended claims and, unless so claimed, the device is not limited to a particular surgical application.

One embodiment provides an apparatus and device for patella fractures. Patella fractures account for 1% of all fractures in adults, with the highest incidence in men between the ages of 20 and 50 years. Most fractures occur from direct force applied to the distal femur with the knee in flexion with common mechanisms being falls and motor vehicle collisions. Operative treatment is indicated in cases of open fracture, severe intraarticular comminution, disruption of the extensor mechanism, and articular displacement of greater than 2-3 mm. Many methods of patella fracture fixation have been proposed in the literature and include a variety of screw designs, Kirschner wires, compressive pins, stainless steel wire, braided suture, locking and non-locking plates, external fixators, and various combinations of these implants. Partial patellectomy with repair of disrupted soft tissue attachments is indicated when the fracture fragments are too small for fixation. Complete patellectomy is an option for severely comminuted fractures but is less common these days as patellofemoral arthroplasty offers the potential for late reconstruction if there is adequate bone remaining. Late complete patellectomy is still an option as well, if necessary.

A well accepted construct for fixation of simple transverse patella fractures is an anterior tension-hand with steel wires passed through partially threaded cannulated screws. This technique results in effective union rates for simple two-part fractures but fixation for more complex and comminuted fracture patterns may require additional modes of fixation. The need for removal of symptomatic implants in tension-band wire constructs has been reported in up to 52% of cases. This appears to be, in part, due to the subcutaneous nature of the patella, making it vulnerable to postoperative irritation, as it can be difficult to sufficiently bury the prominent twisted ends of the steel wires.

Another study showed that current fixation techniques in patients less than 60 years old result in removal of implants in 40% of cases and recommends developing newer techniques to diminish skin irritation. The use of K-wires has been associated with a higher rate of loss of fixation with or without a tension-band construct Loss of fixation requiring operative revision has been reported in 8 to 12% of patella fractures treated with traditional steel wire tension-band constructs augmented with screws. The rate of failure increases to over 20% when K-wires are used instead of screws. This unacceptably high rate of secondary surgeries inspired an investigation as to the use of low-profile titanium mesh plating as an alternative to tension-band wiring. Titanium mesh is a biologically inert and effective implant commonly used in craniomaxillofacial surgery as a buttress for fracture fixation. It is contoured easily, has multiple holes for screw placement, and is has low profile, which is necessary for subcutaneou implantation.

One embodiment of the invention provides a stable, low-profile alternative option for fixation of simple transverse patella fractures. An advantage of using a mesh plate which may be made of titanium, over tension-band for this type of fixation is the potential to lower the rate of secondary surgeries for removal of prominent implants. Another is that it offers more reliable fixation of specific fracture patterns such as coronally oriented fractures. The multiple screws holes within the mesh provide multiple options for screw placement to capture comminuted fragments as well.

The efficacy of one embodiment of the present invention was confirmed by a biomechanical investigation that compared the stiffness and strength of a traditional tension-band wire construct to a low-profile mesh plate and screws that was originally designed for craniomaxillofacial fixation (Universal Neuro 2 Cranial Fixation System, Stryker Osteosynthesis, Germany). The investigation established that a mesh plate could be used as a reliable low-profile alternative to traditional patella fixation techniques.

Twenty-four synthetic medium left patellae with simulated transverse fracture were used. Twelve specimens were fixed with stainless steel wires passed through cannulated screws and crossed the osteotomy site anteriorly in a figure-of-eight fashion. Twelve specimens had 0.6 mm thick titanium mesh fixed to the anterior surface of the specimen with four 13 mm screws. In addition, for applications where additional reinforcement of portions of the mesh may be needed, the thickness of the mesh may he increased in those areas. For example, at the center of the mesh where destructive forces may be the greatest, the thickness of the material may be increased with a gradual tapering of the thickness towards the outer periphery of the mesh.

A custom test fixture was developed to simulate a knee with attached extensor mechanism at 90 degrees of flexion. Loads were applied at a rate of 2 mm/s. Outcome measures were construct stiffness and ultimate force at failure.

Mean stiffness and ultimate strength between constructs was not significantly different ($p=0.94$ and $p=0.63$, respectively). Mean fracture gap distance for the titanium mesh constructs immediately prior to failure was significantly smaller than tension-band wire constructs. Table 1 below provides a comparison of performance results for mean stiffness, ultimate force and gap displacement for the constructs investigated.

|  | Mean Stiffness (N/mm) | Mean Ultimate Failure Force (N) | Mean Gap Displacement (mm) |
| --- | --- | --- | --- |
| Tension-band wire | 19.42 ± 1.34 | 624.66 ± 99.99 | 1.35 ± 0.83 |
| Titanium mesh | 19.49 ± 1.35 | 601.67 ± 135.04 | 2.97 ± 1.53 |
| p-value | 0.94 | 0.63 | 0.02 |

The investigation showed that anteriorly placed mesh plating is a viable alternative to tension-kind wiring for treatment of transverse patellar fractures. However, the investigation unexpectedly showed that the cranial fixation mesh used was found to he incapable of providing a needed tension load capacity and showed limited stability. Pre-failure image analysis of the titanium mesh constructs investigated revealed that fragment displacement occurred due to the expansion of crimped segments that lie in the direction of tensile forces.

Other embodiments of the present invention overcome the above noted deficiencies in the tested mesh. These embodiments provide a high-tension mesh that reduces bone non-union, gaps between the fragments, and provides for the compression of fragments. These embodiments provide a fixation device and method fir the subcutaneous fixation of bone fragments. A mesh plate is formed by the intersection of a plurality of linear legs that are interconnected to form linear lines or rows of legs, which may be in the sagittal plane, and a plurality of crimped legs that are interconnected to form lines or rows of legs, which may be in the transverse plane. The mesh resists expansive forces that are created in the linear lines and a compressive stress is created in the opposingly located, intersecting lines formed by the non-linear legs when tensile loads are applied to the linear lines. This results in a device that minimizes the gap distance between bone fragments by limiting the gap distance to 3 millimeters or less.

As shown in FIGS. 1-4, alternate embodiments of the invention provided enhanced resistance to vertical displacement by eliminating crimped segments in the direction of tensile loading and replacing the segments with, among other things, linear segments or legs. An added advantage of the embodiments is an ability to provide compressive stress in the transverse plane under applied tensile loads in the sagittal plane. This enables comprehensive fracture reduction in highly comminuted bone. Of course, the present invention also covers positioning the linear lines in other planes depending on the situation presented during the procedure.

Figure 1:
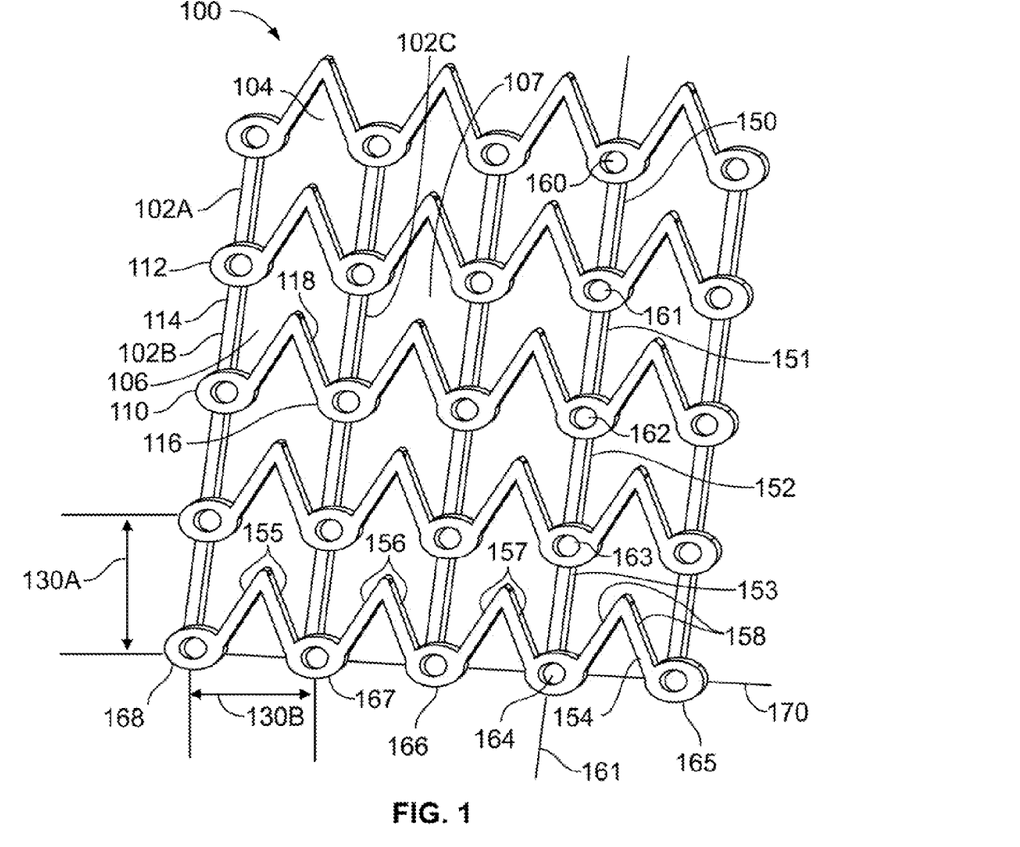
FIG. 1 is a plan view of a first embodiment of the present invention.
Figure 2:
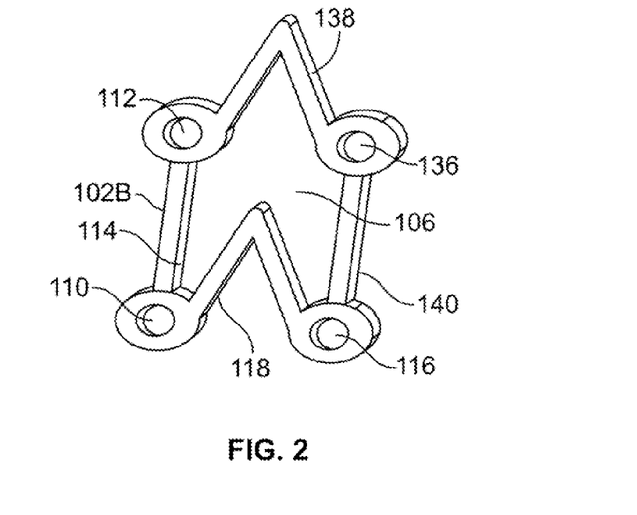
FIG. 2 is an exploded view of a portion of the embodiment shown in FIG. 1.

As shown in FIGS. 1 and 2, one embodiment of the present invention comprises a mesh plate 100 that acts as a fixation device that has a: 1) low-profile; 2) acts as fracture buttress; 3) can resist high tensile forces; 4) can be easily formed to precisely fit the bony contour; 5) applies or provides compressive forces to opposingly located lines formed by non-linear segments when the linear segments are under tensile loads; and 6) offers positionable points of screw fixation to capture multiple fracture fragments.

Plate 100 includes a plurality of repeating patterns 102A-102C that define openings 104, 106 and 107. Pattern 102B illustrates a repeatable unit which may be comprised of a central screw hole 110 connected to a first screw hole 112 by a linear leg 114, which may also be non-linear, and connected to a second screw hole 116 by a crimped or non-linear leg 118, which may be chevron-shaped, curved and configured in other patterns. Segment 102B is further arranged such that the central, first and second screw holes are aligned to form a right angle as demonstrated by lines 130A and 130B. Of course the angular arrangement need not be a right angle and may be an acute or obtuse angle.

As is also shown, because the repeating segments form a pattern, the screw holes may serve alternating functions in the segment. For example, screw hole 112 is designated as a first screw as described above but, as is also shown, it serves as a central screw hole in another repeating segment.

In an alternate embodiment, segments 102A-102C illustrate how three segments may be interconnected to create a quadrilateral shape as shown in FIG. 2. The pattern has two opposing linear legs 114 and 140 and two opposing chevron-shaped legs 118 and 138 that connect screw holes 110, 112, 116 and 136.

In yet another embodiment, a plurality of linear legs, as illustrated by segments 150-153, interconnect a plurality of screw holes 160-164 in a sagittal plane to form linear line 161. In addition, a plurality of crimped legs 155-158, which may be chevron-shaped, interconnect screw holes 164-168 in a transverse plane to form transverse line or crimped line 170. Arranging plate 100 in this manner causes a compressive stress to be created in transverse line or crimped line 170, as well as the other illustrated transverse lines, when tensile loads are applied to sagittal line 161 as well, as one or more of the other sagittal lines.

For plate 100 the distance between the screw holes connected by a linear leg, as shown by line 130A, divided by the distance between the screw holes connected by a crimped leg, as shown by segment 130B, is greater than one when a transverse line 170 is in a fully compressed position. The use of crimped segments, such a chevron-shaped legs, allows for the horizontal expansion of the mesh so as to capture and preload bone fragments.

In other embodiments, the linear lines and crimped lines need not be in the sagittal and transverse planes or be at the angles shown in FIGS. 1 and 2. Other planes and angular displacements may be used so long as the lines intersect to form a mesh and, depending on the needs of the situation in which the mesh is used, other planes may be used as well.

In other embodiments, the screw holes may be circular, oblong and in other configurations that allow for the passage of a screw. In addition, screw holes need not be used at all points of intersection. Nor does plate 100 require the use of the same repeating pattern throughout the plate.

Figure 3:
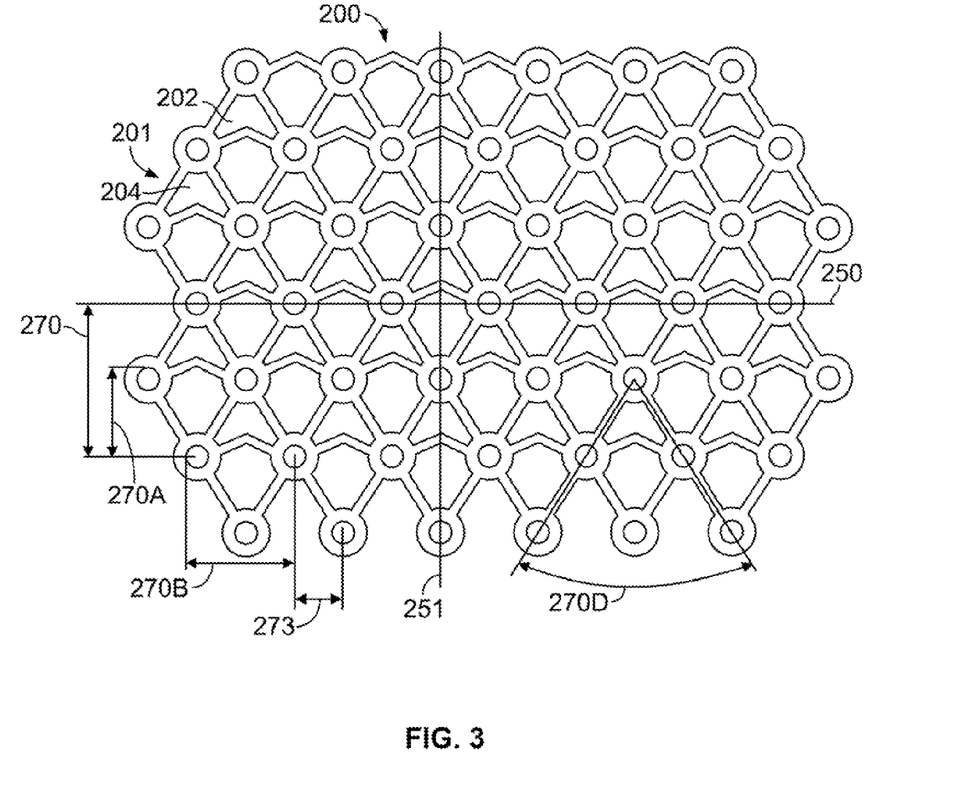
FIG. 3 is a perspective view of an alternate embodiment of the invention.
Figure 4A:
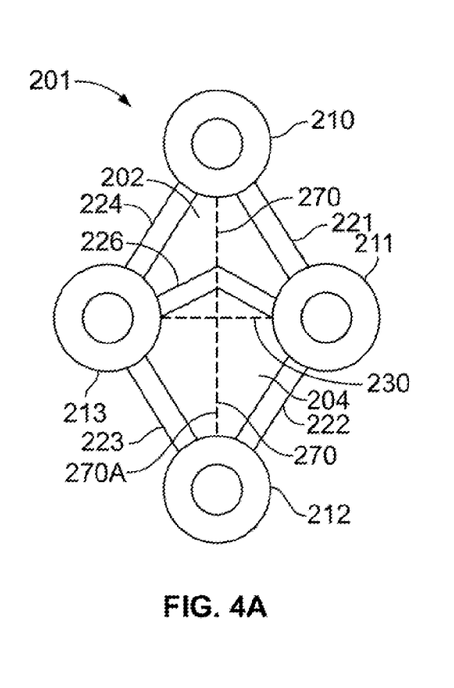
FIG. 4A is an exploded view of a portion of the embodiment shown in FIG. 3 in a neutral state.
Figure 4B:
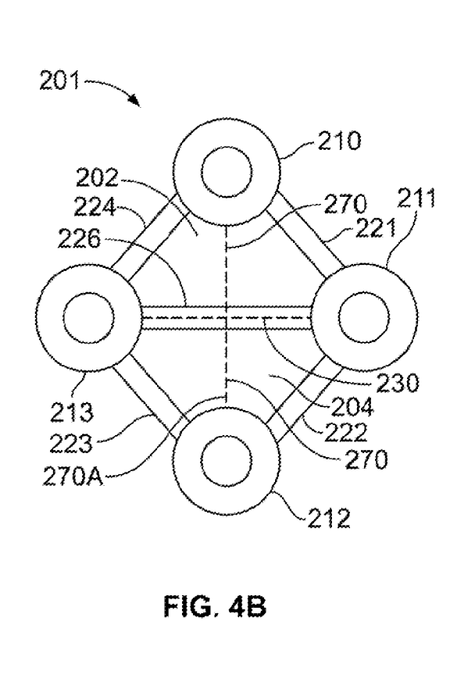
FIG. 4B is an exploded view of a portion of the embodiment shown in FIG. 3 in a stretched or extended state.
Figure 4C:
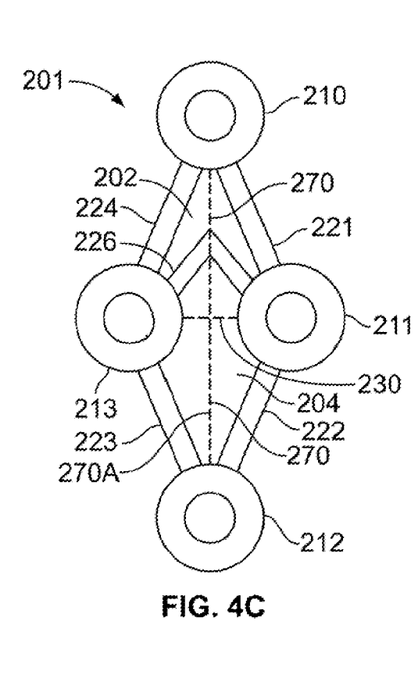
FIG. 4C is an exploded view of a portion of the embodiment shown in FIG. 3 in a squeezed pressed state.

In yet another embodiment, as shown in FIGS. 3 and 4, plate 200 is provided as the fixation device for the subcutaneous fixation of bone fragments. Plate 200 is comprised of a mesh having multiple openings 202 and 204 formed by a repeating rhombic pattern 201 defined by a plurality of vertices, sides and diagonals. As shown, rhombic pattern 201 includes vertices 210-213, which as described above, may be screw holes or points of solid contact, interconnected by linear legs 221-223 located along the sides of the rhombus. Also included is a non-linear leg 226, which may be, crimped, chevron-shaped, curved and in other patterns, that cross-connects non-adjacent screw holes 211 and 213 along a diagonal 230 of the rhombic pattern.

The rhombic patterns of plate 200 may have diagonals that are equal in length or, as shown, diagonal 230 is shorter in length than diagonal 270. As is also shown, the non-adjacent vertices or screw holes are cross-connected by crimped or chevron-shaped legs and aligned along the shorter diagonals along a transverse plane to form transverse line or crimped/non-linear line 250, as well as other lines. On a sagittal plane, vertices are aligned to form sagittal line or linear line 251, as well as other lines.

Arranging plate 200 in this manner causes a compressive stress to be created in transverse line 250, as well as the other illustrated, transverse lines, when tensile loads are applied to sagittal line 251 as well as one or more of the other sagittal lines. In another embodiment, the vertices in the sagittal planes need not being interconnected by linear segments. This causes a compressive stress to be created in sagittal line 250, as well as the other illustrated sagittal lines, when tensile loads are applied to one or more transverse lines 251.

When plate 200 is in a fully expanded position, one half the length of the longer diagonal 270A divided by the length of the shorter diagonal 270B is less than one, but greater than one-half. When plate 200 is in a fully compressed position, one half the length of the longer diagonal 270A divided by the length of the shorter diagonal 270B is greater than one and the angle 270D of the vertices located along the longer diagonals are less than 90 degrees.

In other embodiments, the linear lines and non-linear or crimped lines need not be in the sagittal and transverse planes or be at the angles shown in FIGS. 3 and 4. Other planes and angular displacements may be used so long as the lines intersect to form a mesh and, depending on the needs of the situation in which the mesh is used, other planes may be used as well.

The screw holes are designed to fit orthopedic standard mesh screw sizes, but are not limited to circular holes as described above. Using oblong holes allows for compression of fractures.

The mesh plates are not limited to stainless steel or titanium alloys but can be produced from polymeric or metallic biomaterials. Bioabsorbable mesh plates may be made from polymeric materials such as polyethylene and polypropylene with functional polymeric additives such as glycolic, lactic, and/or fumaric acid. This material may be used as temporizing fixation with material degradation tuned to occur at the same rate as bone formation. These implants would allow for bony union without the long-term potential effects from metallic implant corrosion or breakdown.

In addition, the mesh may be made from stainless steel wire, braided fibers, and composites of the above as well as other materials and structures that imbue flexibility and pliability.

The mesh plates may be fabricated in two forms. In one embodiment, the mesh may be contoured to match the anatomical structure of the bones to be repaired. This reduces surgical time, which may limit the potential for intraoperative complications and reduce surgical costs. The mesh may also be fabricated as sheets to allow for patient-specific contouring to an anatomical region. It allows a user to use the mesh in other areas of repair experiencing high-tension loads that are not listed above.

Figure 5:
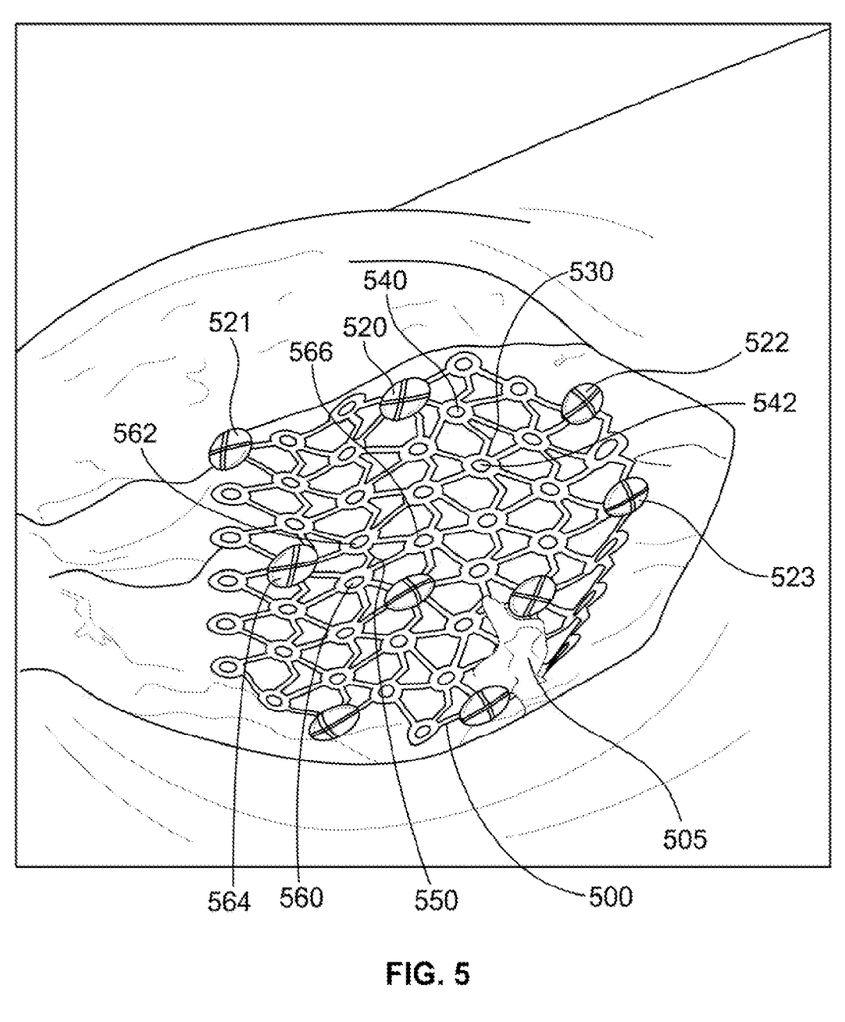
FIG. 5 shows the use of an embodiment of the present invention.

The present invention also provides a method of repairing a fractured patella comprising the steps of subcutaneously inserting a mesh plate 500, as shown in FIG. 5, over said fractured patella. The mesh plate may he of known designs as well as the embodiments described above. Surgical screws 520-523 affix plate 500 to fractured patella 505 in order to create fracture gaps that are less than 3 millimeters. Using the mesh described above further includes the step of creating compressive forces in a transverse plane by applying tensile forces in the sagittal planeto create fracture gaps that are less than 3 millimeters.

The above steps may also be used to repair fragmented bone in other anatomical areas such as the sternum and ulna. Moreover, for any given procedure, other planes and angular displacements may he used so long as the lines intersect to form a mesh and, depending on the needs of the situation in which the mesh is used, other planes may be used as well.

For the embodiment shown in FIGS. 1 and 2, the non-linear nature of segments 118 and 138 permit the segments to flex thereby allowing opposingly located screw holes 112 and 136 and 110 and 116 to be extended away from each other; thus stretching the associated portion of the mesh outwardly. Conversely, the non-linear nature of segments 118 and 138 also permit opposingly located screw holes 112 and 136 and 110 and 116 to be retracted towards one another; thus squeezing the associated portion of the mesh together.

Similarly, for the embodiment shown in FIGS. 3 and 4A-4C, the non-linear nature of segment 226 permits the segment to flex thereby allowing opposingly located screw holes 211 and 213 to be extended away from each other; thus stretching the associated portion of the mesh outwardly. Conversely, the non-linear nature of segment 226 also permits the opposingly located screw holes to be retracted towards one another; thus squeezing the associated portion of the mesh together.

In addition, as is further shown, linear segments 221-224, combine to form non-linear segments that flex and thereby allowing opposingly located screw holes 210 and 212 to be extended away from each other; thus stretching the associated portion of the mesh outwardly. Conversely, the non-linear nature of the segments also permits the opposingly located screw holes to he retracted towards one another; thus squeezing the associated portion of the mesh together.

FIG. 5 illustrates how the design of the embodiments described above may he manipulated to permit a user to contour the mesh to fit an anatomical structure. The non-linear segments permit portions of the mesh to be stretched and or compressed into a desired shape. In addition, the ability of the mesh to stretch outwardly or to compress inwardly further allows the mesh to be curved in order to complement an anatomical structure. For example, segment 530 may he extended outwardly thereby transitioning the segment from a non-linear configuration into a longer linear segment and causing screw holes 540 and 542 to extend away from one another to adapt to a curvature or to locate a screw in a desired position. In other portions of mesh 500, segment 550 may be retracted inwardly, shortening its length, and thereby causing screw holes 560 and 562 to retract towards another. This also may cause screw holes 566 and 564 to extend away from one another. Again, this allows the mesh to adapt to a curvature or to locate a screw in a desired position The ability to flex the mesh by stretching or squeezing it allows it to be contoured to fit non-planar structures. It also allows for the manipulation and positioning of the screw holes to accommodate the affixation of anatomical. structures that may otherwise not be conveniently located with respect to a given screw hole. It also allows the mesh to be stretched outwardly and to then utilize any inherent retraction in the segments to create a compressive force that minimizes any gaps between the bone fragments by compressing the fragments together.

What is claimed is:

1. A method of repairing a fractured patella having a plurality of bone fragments separated by fracture gaps comprising the steps of:
   subcutaneously inserting a fixation mesh over a portion of the fractured patella, said mesh plate having one or more repeating segments that define a plurality of openings;
   said one or more repeating segments comprising a central screw hole connected to a first screw hole by a linear leg and connected to a second screw hole by a non-linear leg; and affixing said fixation mesh to the fractured patella fragments using screws so that said central screw hole and said second screw hole are positionable inwardly and outwardly with respect to each other so as to urge one or more fragments towards or away from one another.

2. The method of claim 1, wherein said one or more repeating segments includes a non-linear segment.

3. The method of claim 2, wherein said non-linear segment is crimped, curved or chevron-shaped.

4. The method of claim 1, wherein said central, first and second screw holes are aligned to form a right angle.

5. The method of claim 1, wherein said central, first and second screw holes are aligned to form an acute angle.

6. The method of claim 1, wherein a repeating pattern is created by three interconnected repeating segments.

7. The method of claim 1, wherein the fracture gaps between bone fragments are limited to 3 millimeters or less.

8. The method of claim 1, wherein said mesh is flexible and has a thickness that reduces from a central area to edges of said mesh.

9. The method of claim 1, wherein a plurality of linear segments are interconnected to form lines of segments and a plurality of non-linear segments are interconnected to form lines of segments, wherein compressive stress is created in said non-linear segments when tensile loads are applied to said linear segments and resisting expansive forces in said linear segments.

10. The method of claim 9, wherein a distance between the screw holes connected by a linear segment divided by a distance between said screw holes connected by said non-linear segment is greater than one when a line of said linear segments is in a fully compressed position.

11. A method of repairing a fractured patella having a plurality of bone fragments separated by fracture gaps comprising the steps of:
   subcutaneously inserting a fixation mesh over a portion of the fractured patella, said mesh having a repeating rhombic pattern defined by a plurality of vertices, sides and diagonals defining a plurality of openings and screw holes;
   said screw holes located at one or more of said vertices, said screw holes interconnected by linear segments located along said sides;

a plurality of non-linear segments cross-connecting non-adjacent screw holes along a diagonal of said rhombic pattern; and affixing said fixation mesh to the fractured patella fragments using screws so that said screw holes are positionable inwardly and outwardly with respect to each other.

12. The method of claim 11, wherein said non-liner segments are crimped, curved or chevron-shaped.

13. The method of claim 11, wherein said diagonals are equal in length.

14. The method of claim 11, wherein said diagonals are unequal in length with one diagonal being shorter in length than another diagonal.

15. The method of claim 14, wherein said non-adjacent screw holes are cross-connected by said non-linear segments and aligned along said shorter diagonal to form lines of interconnected segments, and said screw holes are aligned along lines formed by said linear segments, wherein compressive stress is created in lines created by said non-linear segments when a tensile load is applied to a line created by said linear segments and resisting expansive forces in said lines created by said non-linear segments.

16. The method of claim 15, wherein, when said mesh is in a fully expanded position, one half of a length of the longer diagonal divided by a length of the shorter diagonal is less than one, but greater than one-half and when said mesh is in a fully compressed position, one half the length of the longer diagonal divided by the length of the shorter diagonal is greater than one and an angle of the vertices located along the longer diagonals are less than 90 degrees.

17. The method of claim 11, wherein the fracture gaps between bone fragments are limited to 3 millimeters or less.

18. The method of claim 11, wherein said mesh is flexible and has thickness that reduces from a central area to edges of said mesh.

19. A method of repairing a fractured patella having a plurality of bone fragments separated by fracture gaps comprising the steps of:

subcutaneously inserting a fixation mesh over a portion of the fractured patella;

said fixation mesh having a plurality of screw holes interconnected by linear segments forming linear lines along sagittal planes;

a plurality of screw holes interconnected by non-linear segments forming lines along transverse planes; and affixing said fixation mesh to said fractured patella fragments using screws to maintian fracture gaps to distances that are 3 millimeters or less.

20. The method of claim 19, further including the step of creating compressive forces in said transverse planes by applying tensile forces in said sagittal planes and resisting expansive forces in said linear lines.

21. The method of claim 19, wherein a compressive force is created by outwardly extending a screw hole towards a fragment, affixing said mesh to said fragment while said screw hole is outwardly extended, permitting said mesh to retract to create a compressive force.

22. The method of claim 19, wherein said mesh is flexible and has thickness that reduces from a central area to edges of said mesh.

* * * * *